United States Patent [19]

Steer

[11] Patent Number: 4,714,465
[45] Date of Patent: Dec. 22, 1987

[54] UROSTOMY APPLIANCE

[75] Inventor: Peter L. Steer, Surrey, England

[73] Assignee: Craig Medical Products Ltd., Sussex, England

[21] Appl. No.: 863,817

[22] Filed: May 12, 1986

Related U.S. Application Data

[63] Continuation of Ser. No. 633,725, Jul. 23, 1984, abandoned.

[30] Foreign Application Priority Data

Aug. 22, 1983 [GB] United Kingdom ............... 8322544

[51] Int. Cl.⁴ .............................................. A61F 5/44
[52] U.S. Cl. .................................................... 604/340
[58] Field of Search ................................ 604/332–345

[56] References Cited

U.S. PATENT DOCUMENTS

| 2,703,576 | 3/1955 | Furr, Jr. | 128/283 |
| 3,074,404 | 1/1963 | Robinson | 128/283 |
| 3,331,370 | 7/1967 | Notley, Sr. | 604/344 |
| 3,373,745 | 3/1968 | Benfield et al. | 128/283 |
| 3,520,301 | 7/1970 | Fenton | 604/338 |
| 3,878,847 | 4/1975 | Mavsan | 604/338 |
| 4,121,589 | 10/1978 | McDonnell | 128/283 |
| 4,219,023 | 8/1980 | Galindo | 604/344 |
| 4,319,571 | 3/1982 | Winchell | 128/283 |
| 4,356,819 | 11/1982 | Potaczek | 604/334 |
| 4,387,712 | 6/1983 | Briggs et al. | 604/333 |
| 4,387,713 | 6/1983 | Calanni | 604/336 |

FOREIGN PATENT DOCUMENTS

| 1295252 | 11/1972 | United Kingdom | 604/333 |
| 2041753 | 9/1980 | United Kingdom | 604/336 |

Primary Examiner—C. Fred Rosenbaum
Assistant Examiner—J. L. Kruter
Attorney, Agent, or Firm—Lawrence S. Levinson; Robert E. Lee, Jr.

[57] ABSTRACT

A one-piece urostomy appliance has a drainage bag secured to an apertured flange which is in turn secured to an apertured adhesive pad. The body side of the apertured flange has a flexible skirt encircling the stoma aperture and located adjacent the radially inner boundary of the adhesive pad. The skirt is constructed and located to impede leakage of urine towards the adhesive pad.

2 Claims, 2 Drawing Figures

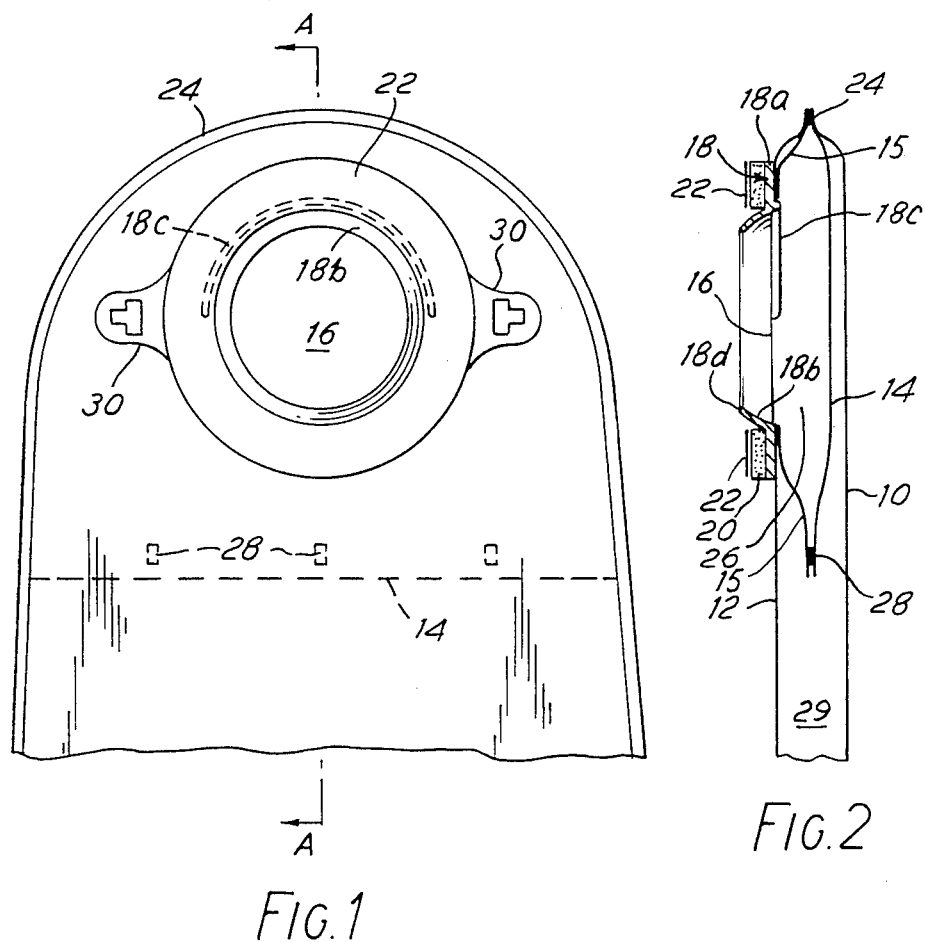

UROSTOMY APPLIANCE

This is a continuation of co-pending application Ser. No. 633,725 filed on July 23, 1984 now abandoned.

BACKGROUND OF THE INVENTION

This invention relates to an urostomy appliance.

Urostomy appliances are known. They consist of a bag to receive discharged urine and means for fixing the bag to the wearer. While some known appliances are satisfactory from some points of view, it would be desirable from the points of view of economy and simplicity to have a one piece appliance in which the possibility of migration of urine to the adhesive is minimized, and in which the possibility of ulceration of the skin in the region of the adhesive is also minimized.

SUMMARY OF THE INVENTION

According to the invention, there is provided a one-piece urostomy appliance comprising a drainage bag secured to an apertured flange which is in turn secured to an apertured adhesive pad, the body side of the apertured flange being provided with a flexible skirt encircling the stoma aperture and located adjacent the radially inner boundary of the adhesive pad, the skirt being located to impede leakage of urine towards the adhesive pad.

According to a preferred embodiment of the invention, in such a one-piece urostomy appliance, the apertured flange has an arcuate rib or hood which extends into the bag and is intended to keep the front wall or any internal walls of the bag away from the stoma of the user so as to help good drainage and to help to avoid discomfort.

The invention will be better understood from the following description of an illustrative example, given with reference to the accompanying drawings in which:

BRIEF DESCRIPTION OF THE DRAWINGS

FIG. 1 is a front view of one example of a urostomy appliance according to the invention; and FIG. 2 is a cross-section on the line A—A of FIG. 1.

DETAILED DESCRIPTION OF THE DRAWINGS

The urostomy appliance illustrated in FIGS. 1 and 2 has a front wall 10 secured to a rear wall 12 there also being internal walls 14 and 15 for a reason which will be later described. The rear wall 12 has a stomal aperture therein that is to say there is a hole, usually circular, in an upper portion of the wall 12. An apertured flange 18 is secured to the external surface of the wall 12 surrounding the aperture 16; it may be secured by heat welding or by adhesive or in any other suitable manner. The flange 18 has a flat portion 18a and a flexible skirt portion 18b extending from the rim of the flange aperture towards the skin of the wearer (when the bag is in its normal worn position). The flange 18 also has a semi-circular rib 18c on its surface which faces towards the interior of the bag. Attached to the flange 18, on its side opposite to the side to which the bag is attached, is an annular pad 20 of medical grade adhesive material. Suitable materials are those sold under the trade names "Stomahesive" and "Urihesive" by E. R. Squibb & Sons Inc. or subsidiary companies. The skirt portion of 18b extends through the stomal aperture in the pad 20 to be raised above (e.g. 0.5 to 1.0 mm) the skin-contacting surface of the pad 20. On the surface of the adhesive pad 20 which will engage the body of the wearer in use, there is a manually strippable protective layer 22.

As is conventional in drainage bags and urostomy bags, the walls 10 and 12 are of plastics material and are secured together around their periphery, for example by plastics welding or by adhesive. A weld is shown at 24 in FIG. 2. The internal walls 14 and 15, the latter having a hole corresponding to the hole 16, define a compartment 26 into which discharged liquid, e.g. urine, first passes, and the lower region of the wall 14 is united to the lower region of wall 15 by a plurality of spaced weld joints 28. Consequently the exit path for liquid from the compartment 26 is between these joints 28 and into the lower part 29 of the bag.

The flange 18 has two "ears" shown at 30, by which if desired a belt or strap harness support can be attached to the bag. In general, no such harness will be needed as the adhesive effect of the pad 20 will be sufficient to retain the urostomy appliance in position on the wearer.

The flexible skirt 18b serves an important function in that its rim 18d makes sealing contact with the skin of the wearer around the stoma, so tending to preclude any urine from leaking to a region where it can effect and degrade the adhesive pad 20. With prior known designs of urostomy appliances, reduction in security of attachment due to the effect of urine upon an adhesive pad has been a serious disadvantage. In addition, the flexible skirt 18b tends to prevent urine leaking to the surface of the patient's skin and so minimizes irritation.

An arcuate rib or hood 18c is illustrated which is generally semi-circular and extends into the chamber 26. Its function is to hold any wall of the bag which may overlap the stoma, such as inner wall 14 or front wall 10 in the absence of any inner walls, away from the stomal area, so that the urostomy appliance is more comfortable to wear.

The arrangement of internal walls 14 and 15 and the weld joints 28 therebetween serve in use as a non-return valve, allowing urine to drain readily from the chamber 26 into the main part 29 of the bag, but preventing any substantial transfer of urine in the opposite direction if for example a relatively full bag was accidentally squeezed or bumped or otherwise placed under external pressure.

I claim:

1. A one-piece urostomy appliance comprising a drainage bag secured to one side of an apertured flange which is in turn secured on its body side opposite the urostomy appliance to an apertured adhesive pad for securing the appliance to the body of the user, the body side of the apertured flange being provided with a flexible skirt encircling the stoma aperture and located adjacent the radially inner boundary of the adhesive pad, the flexible skirt extending from the rim of the flange aperture through the aperture in the adhesive pad towards the body of the wearer and extending beyond the skin-contacting surface of the adhesive pad on the body side of the pad, the rim of the flexible skirt adapted to make sealing contact with the skin of the body of the wearer spaced apart from and around the stoma to impede leakage of urine towards the inner boundary of the adhesive pad and the surface of the skin of the wearer, said apertured flange further comprising a substantially semi-circular arcuate rib or hood which extends into the bag and is positioned to keep a front or inner wall of the bag away from the stoma of the wearer.

2. An appliance according to claim 1 in which the flexible skirt is raised by about 0.5 to 1.00 mm above the skin-contacting surface of the apertured adhesive pad.

* * * * *